(12) United States Patent
Cruchet et al.

(10) Patent No.: US 7,393,362 B2
(45) Date of Patent: Jul. 1, 2008

(54) HIP PROSTHESIS

(75) Inventors: Patrick Cruchet, Le Mans (FR); Uwe Bunz, Wolfschlugen (DE); Bernard Masson, Pechabou (FR); Paul Silberer, Waghausel (DE); Martin Dietrich, Potenitz (DE)

(73) Assignees: CeramTec AG, Plochingen (DE); Ceramconcept Worldwide L.L.C., Newark, DE (US)

( * ) Notice: Subject to any disclaimer, the term of this patent is extended or adjusted under 35 U.S.C. 154(b) by 493 days.

(21) Appl. No.: 10/768,972

(22) Filed: Jan. 30, 2004

(65) Prior Publication Data

US 2004/0225370 A1     Nov. 11, 2004

(30) Foreign Application Priority Data

Jan. 31, 2003   (DE)  ............................... 103 04 102

(51) Int. Cl.
*A61F 2/32*     (2006.01)
*A61F 2/30*     (2006.01)

(52) U.S. Cl. .................................. 623/22.18; 623/23.56

(58) Field of Classification Search .............. 623/22.18, 623/19.12, 22.16, 22.17, 23.4, 23.56
See application file for complete search history.

(56) References Cited

U.S. PATENT DOCUMENTS

| | | | | |
|---|---|---|---|---|
| 4,678,472 A | * | 7/1987 | Noiles | ........................ 623/23.4 |
| 2002/0116068 A1 | * | 8/2002 | McLean | ................... 623/22.15 |

FOREIGN PATENT DOCUMENTS

EP     0 461 019 B1   *   10/1995

* cited by examiner

*Primary Examiner*—David H. Willse
(74) *Attorney, Agent, or Firm*—Fulbright & Jaworski, L.L.P.

(57) ABSTRACT

A hip prosthesis has a shaft which is implantable in the femur, a ball head anchored on the shaft, a socket in which the ball head is movably supported, and a bipolar shell placed between the ball head and the socket, whereby the ball head rotates in the bipolar shell and the bipolar shell rotates in the socket.

8 Claims, 5 Drawing Sheets

HIP PROSTHESIS

This application claim priority from German 103 04 102.8 filed Jan. 31, 2003, hereby incorporated by reference in its entirety.

FIELD OF THE INVENTION

The invention relates to a hip prosthesis for implantation in humans and animals.

BACKGROUND AND SUMMARY OF THE INVENTION

Known hip prostheses comprise a shaft which is implanted in the femur, and a ball head which is anchored to the shaft by a conical clamp, for example. The ball head rotates in a socket. The socket may be implanted directly in the acetabulum, or may be inserted in an additional outer shell or in plastic sheathing and then implanted.

In the known hip prostheses, a certain tendency toward luxation is always observed; i.e., for certain motions the ball head slides out of the socket. In the medical literature, the percentage tendency for luxation of prosthetic systems such as hip prostheses is in the single digits.

This tendency toward luxation could be counteracted by a raised edge on the socket, or by increasing the slide pairing diameter. The slide pairing diameter of the ball head is determined by the diameter of the outer surface of the ball head which articulates with the socket.

However, various disadvantages result from these structural designs. For example, a raised edge on the socket severely limits the range of motion of the ball head with the shaft in the socket. The use of larger slide pairing diameters, i.e., a larger ball head and a larger socket, is limited by restrictions on the available space.

The object of the invention is to improve the tendency toward luxation in hip prostheses, compared to the prior art.

This object is achieved according to the invention by placing a bipolar shell between the ball head and the socket, whereby the ball head rotates in the bipolar shell and the bipolar shell rotates in the socket. The luxation is greatly reduced by this doubled capability for rotation. This system is also referred to as a "double mobility system."

The ratio of the diameters of the slide pairing of the bipolar shell and the ball head preferably is between 1.05 and 5, preferably between 1.2 and 2.

The slide pairing diameter of the bipolar shell is advantageously between 26 mm and 40 mm, preferably 32 mm, and the slide pairing diameter of the ball head is between 14 mm and 32 mm, preferably 22.2 mm.

For a hip prosthesis having a ceramic ball head, a ceramic bipolar shell, and a ceramic socket, the tribological conditions of the ceramic components are advantageously defined by a combination of the following features:

a) The hardness of the ceramic components is greater than 1,000 HV (Vickers).
b) The surface finishes on the articulating surfaces of the ceramic components have a roughness less than 0.1 μm (Ra value<0.1 μm).
c) The contact angle between the articulating surfaces of the ceramic components is between 1° and 8° (measured in Ringer's solution).
d) The difference in the slide pairing diameters of the articulating surfaces of the ceramic components is between 1 and 200 μm, preferably between 20 and 120 μm.

In one preferred embodiment the centers of rotation of the ball head with respect to the bipolar shell, and of the bipolar shell with respect to the socket, have an offset d which is between 0.1 mm and 5 mm, preferably between 1.5 and 2.5 mm.

In a further preferred embodiment the bipolar shell in cross section has different wall thicknesses, the greatest wall thickness being provided in the region of the opening.

The ball head is held in the bipolar shell by a retaining ring inserted into the bipolar shell at the edge of same.

The advantages of this hip prosthesis are described below in comparison to the prior art.

The range of motion (ROM) is greatly increased compared to systems with a banked socket edge.

The tendency toward luxation is greatly reduced by a wedging effect between the bipolar shell with the retaining ring, and the socket.

The specialized kinematics and tribology result in a motion that is different from simple rotation.

The sequence of motion is as follows:

First there is motion between the ball head and the bipolar shell. If the range of motion of this first sliding surface is expended, for example by the shaft striking against the retaining ring, the second sliding surface between the bipolar shell and the socket is deployed; i.e., the further motion occurs only at the outer sphere of the bipolar shell.

As a result of the defined tribological properties and kinematic conditions, there is no pure rotation about the midpoint of the outer sphere of the bipolar shell, but instead, next there is rotation of the bipolar shell about the midpoint of the ball head. The bipolar shell rotates out of the socket. As a result of this specialized coupled motion there is a wedging effect between the bipolar shell with the retaining ring, and the socket. Luxation is thus made much more difficult, as shown by measurements of the luxation force. As a result, the tendency toward luxation is considerably lower.

Materials of the Prosthetic System:

The prosthesis may be composed of the following materials:
1. Prosthesis shaft (metal, ceramic, plastic), preferably metal
2. Ball head (ceramic, metal, plastic), preferably ceramic
3. Bipolar shell (metal, ceramic, plastic), preferably ceramic
4. Retaining ring (metal, ceramic, plastic), preferably plastic
5. Socket or socket insert (metal, ceramic, plastic), preferably ceramic Further features of the invention become evident from the figures described below:

DETAILED DESCRIPTION

Figure 5:
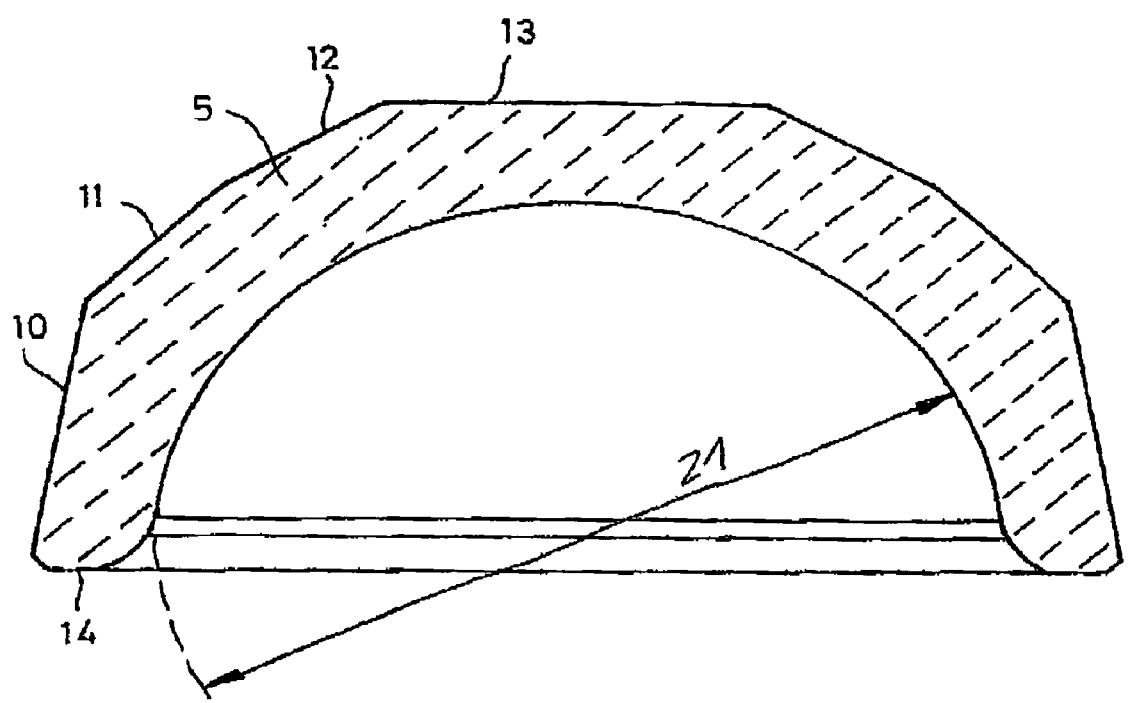
FIG. 5 shows a socket 5.
Figure 6:
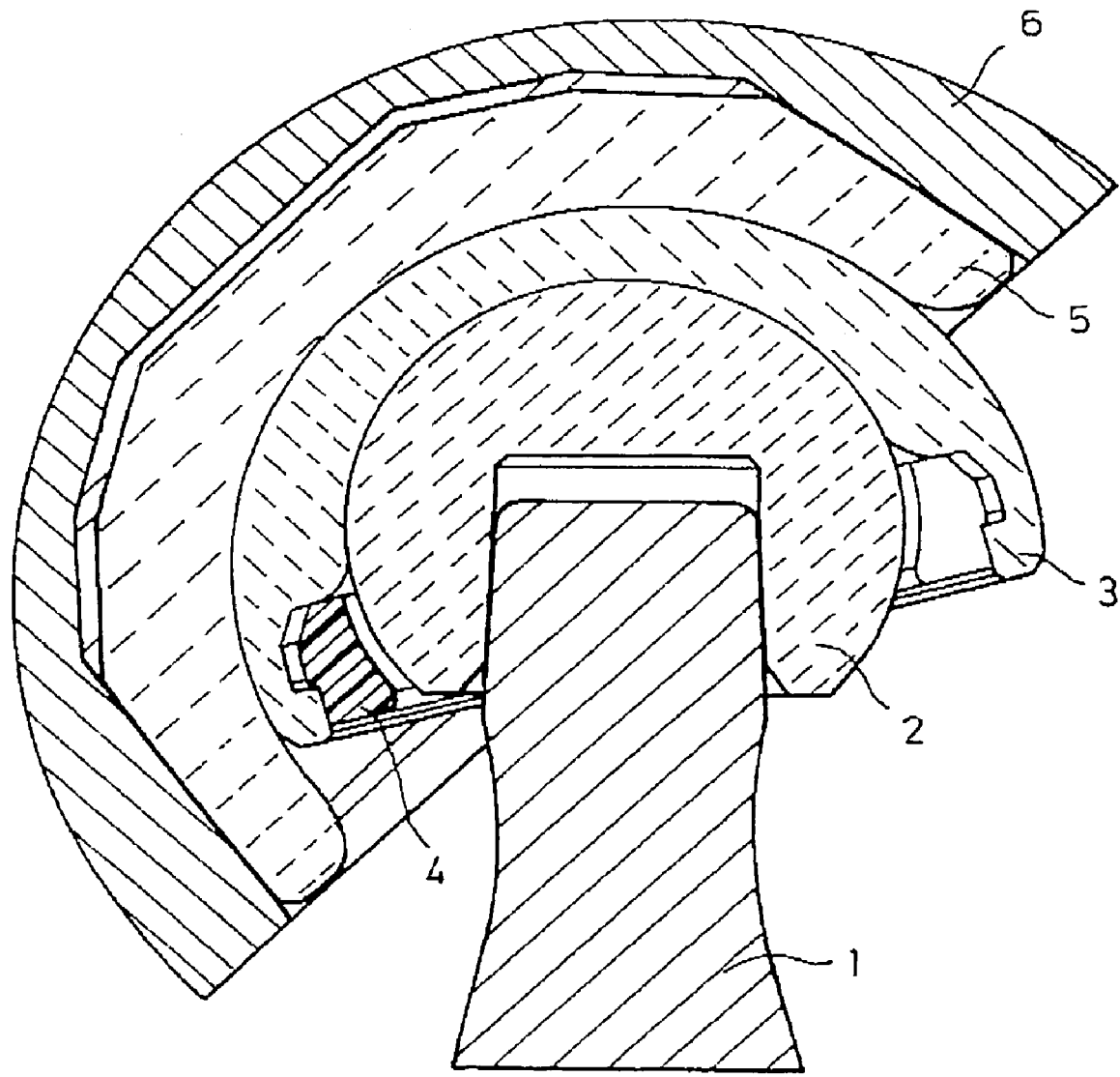
FIG. 6 shows a hip prosthesis.
Figure 7:
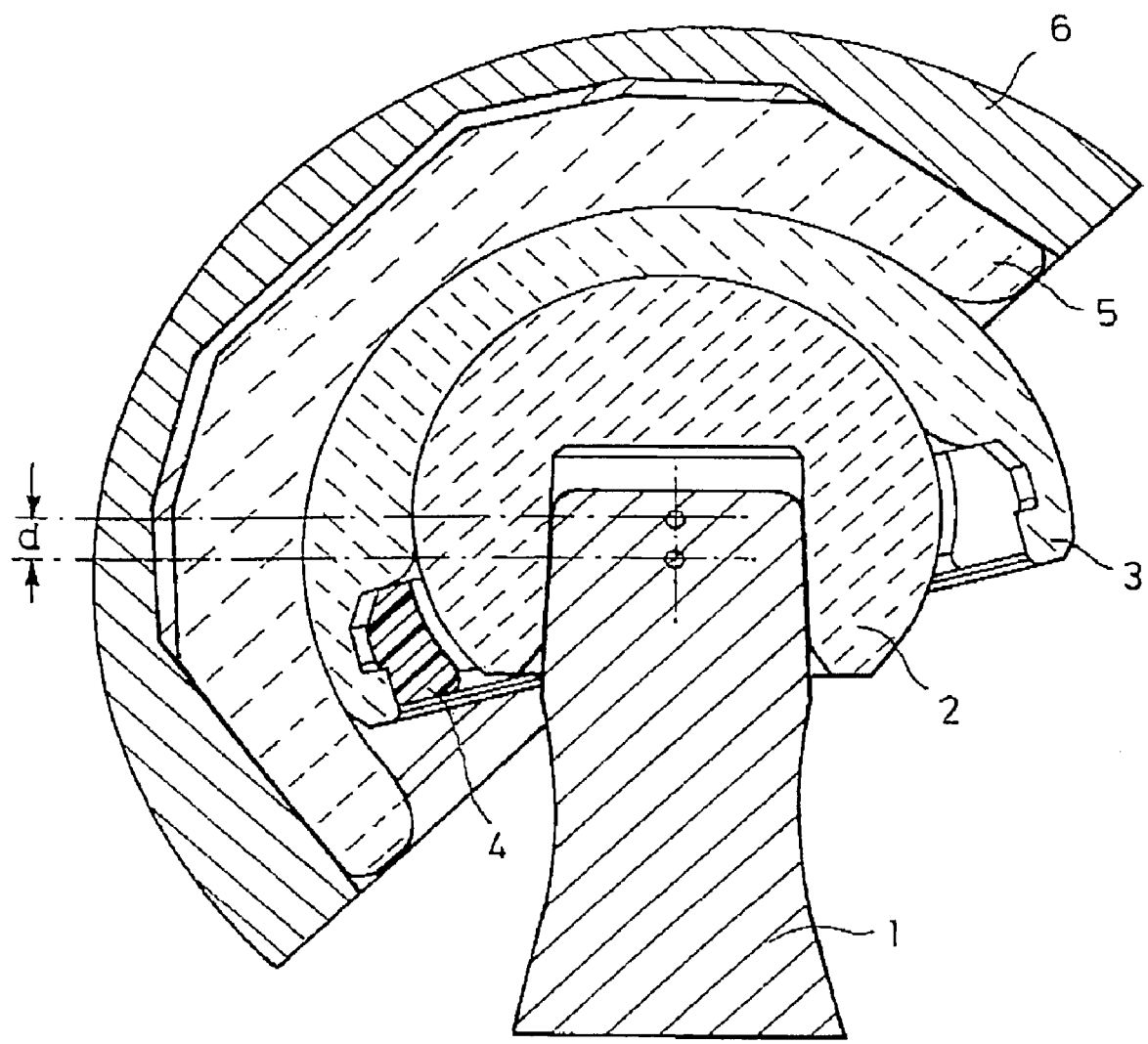
FIG. 7 shows a hip prosthesis with offset d indicated.

FIGS. 1 through 5 show in cross section the individual parts of an inventive embodiment of a hip prosthesis, and FIGS. 6 and 7 show a cross section of a complete hip prosthesis.

Figure 1:
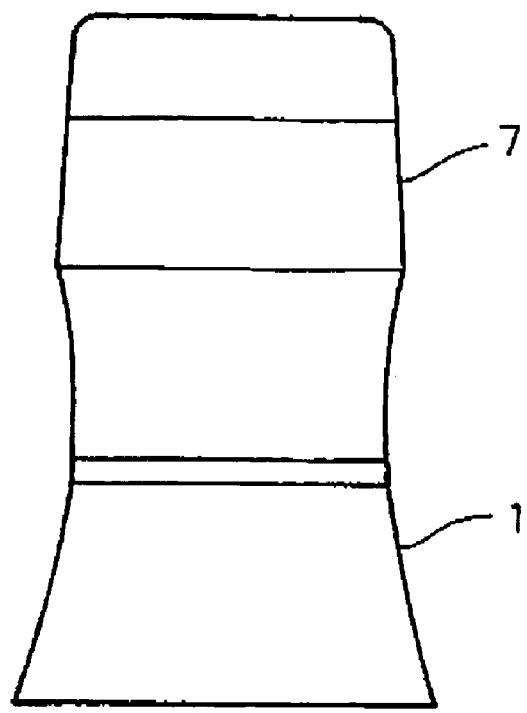
FIG. 1 shows the end of shaft 1 which faces the ball head.
Figure 2:
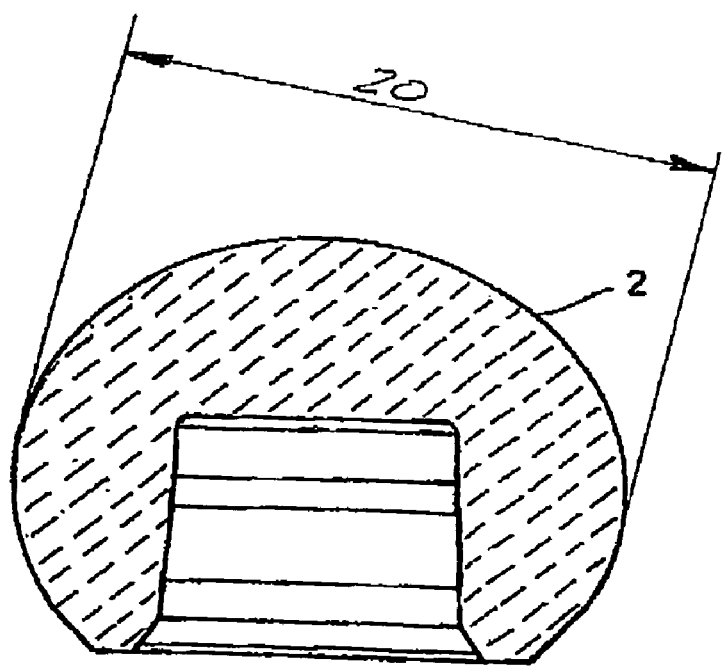
FIG. 2 shows a ball head 2.

FIG. 1 shows the front part of a shaft 1, which with its end not shown is implanted in the femur. The end of shaft 1 shown is provided with a conical surface 7. This conical surface 7 is used for affixing a ball head 2, as shown in FIG. 2. Ball head 2 has a recess, likewise provided with a conical surface on its circumferential surface, so that ball head 2 can be affixed to shaft 1.

Figure 3:
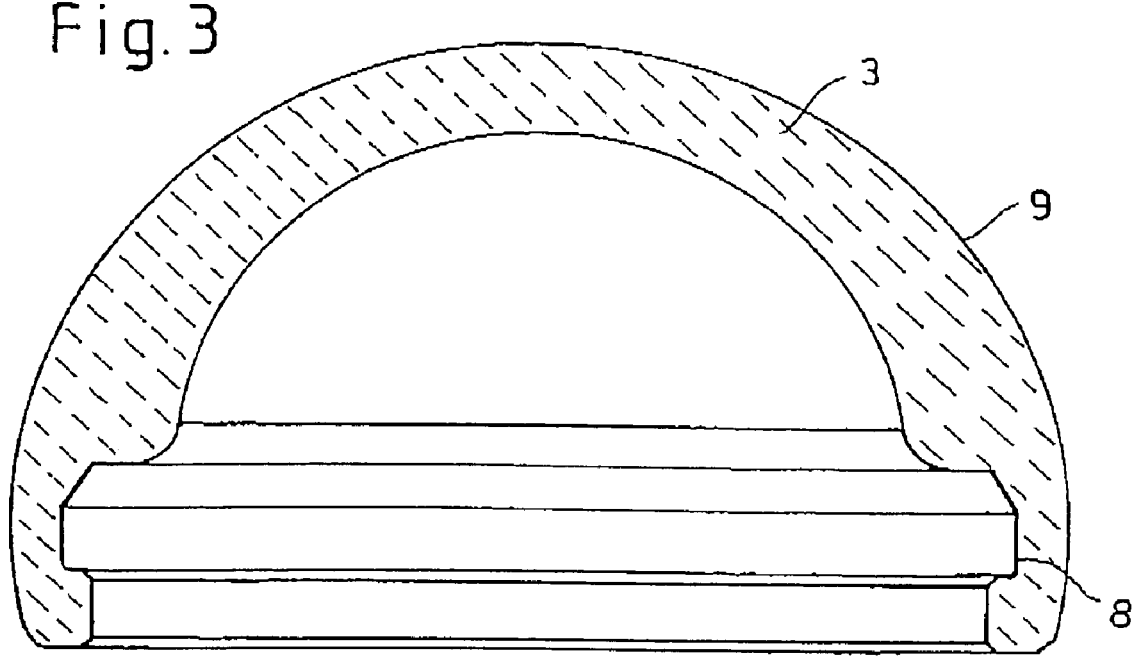
FIG. 3 shows a bipolar shell 3.
Figure 4:
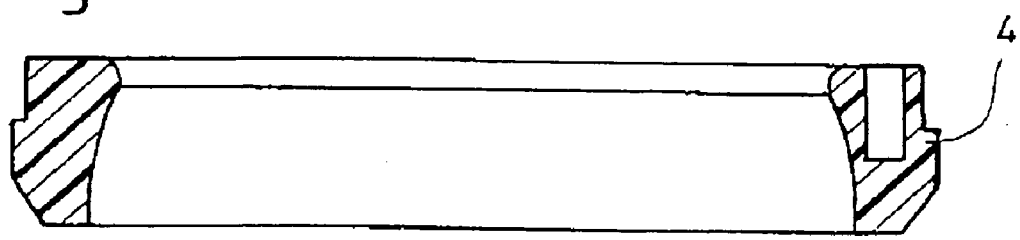
FIG. 4 shows a retaining ring 4 for insertion in bipolar shell 3.

FIG. 3 shows a bipolar shell 3 with a spherical outer surface 9. In the interior of bipolar shell 3, on its side facing the opening, a recess 8 is provided in which a retaining ring 4 (see FIG. 4) can be inserted. This retaining ring 4 is used for affixing ball head 1 in bipolar shell 3.

FIG. 5 shows a socket 5 having a spherical recess which is used to accommodate the bipolar shell shown in FIG. 3. Socket 5 is provided on its outer side with a conical slope 10 which transitions via two flat regions 11, 12 into a flat region 13 running parallel to upper edge 14.

The slide pairing diameter 20 of bipolar shells is shown in FIG. 2. The slide pairing diameter 20 of the bipolar head is shown in FIG. 5. The difference in the slide pairing diameters is the slide pairing diameter 21 of the shell 5 minus the slide pairing diameter 20 of the ball head 2.

FIGS. 6 and 7 show the assembly of the referenced individual components.

In this preferred embodiment, shaft 1 is made of metal (titanium), and ball head 2, bipolar shell 3, and socket 5 are made of ceramic, which are specially processed or manufactured as described above. Outer shell 6 in which socket 5 is inserted is made of metal. This shell 6 may optionally be omitted when socket 5 is implanted directly in the acetabulum. The retaining ring indicated by reference number 4 is made of plastic.

FIG. 7 shows offset d of the centers of rotation of ball head 2—bipolar shell 3 and bipolar shell 3—socket 5.

It is claimed:

1. A hip prosthesis comprising a shaft which is implantable in the femur, a ball head anchored on the shaft, a socket in which the ball head has a slide pairing diameter and is movably supported, and a bipolar shell has a sliding pairing diameter and is placed between the ball head and the socket, whereby the ball head rotates in the bipolar shell and the bipolar shell rotates in the socket, wherein the ratio of the slide pairing diameter of the bipolar shell and the ball head is between 1.05 and 5, wherein the ball head, the bipolar shell, and the socket are ceramic, wherein the tribological conditions of die ceramic components are defined as follows:
    a) the hardness of the ceramic components is greater than 1,000 HV (Vickers);
    b) the surface finishes on the articulating surfaces of the ceramic components have a roughness less than 0.1 μm (Ra value<0.1 μm);
    c) the contact angle between to articulating surfaces of the ceramic components is between 1° and 8° (measured in Ringer's solution); and
    d) the difference in the slide pairing diameters of the articulating surfaces of the ceramic components is between 1 and 200 μm.

2. The hip prosthesis of claim 1, where said differences in the slide pairing diameters is between 20 and 120 microns.

3. The hip prosthesis according to claim 1 wherein the ratio of the diameters of the slide pairing of the bipolar shell and to ball head is 5.

4. The hip prosthesis according to claim 3, wherein the slide pairing diameter of the bipolar shell is between 26 mm and 40 mm, the slide pairing diameter of the ball head is between 14 mm and 32 mm.

5. The hip prosthesis of claim 4, wherein said slide pairing ball, diameter is 22.2 mm.

6. The hip prosthesis according to claim 3, wherein the slide pairing diameter of the bipolar shell is 32 mm.

7. A hip prosthesis comprising a shaft which is implantable in a femur, and ceramic components including a ceramic ball bead anchored on the shaft, a ceramic socket in which the ceramic ball head is movably supported, and a ceramic bipolar shell consisting of a single material, wherein the ceramic bipolar shell is placed between to ceramic ball head and the ceramic socket, wherein the ceramic ball head rotates in and directly contacts the ceramic bipolar shell and the ceramic bipolar shell rotates in the ceramic socket, wherein tribological conditions of the ceramic components are defined by a combination of the following features:
    a) the ceramic components have a hardness of greater than 1,000 HV (Vickers);
    b) the ceramic components have articulating surfaces with surface finishes having a roughness less than 0.1 μm (Ra value<0.1 μm);
    c) the ceramic components have a contact angle between the articulating surfaces of the ceramic components is between 1° and 8° (measured in Ringer's solution); and
    d) slide pairing diameters of the articulating surfaces of the ceramic components have a difference of between 1 and 200 μm.

8. The hip prosthesis of claim 7, where said difference in the slide pairing diameters is between 20 and 120 microns.

* * * * *